Figure 2:
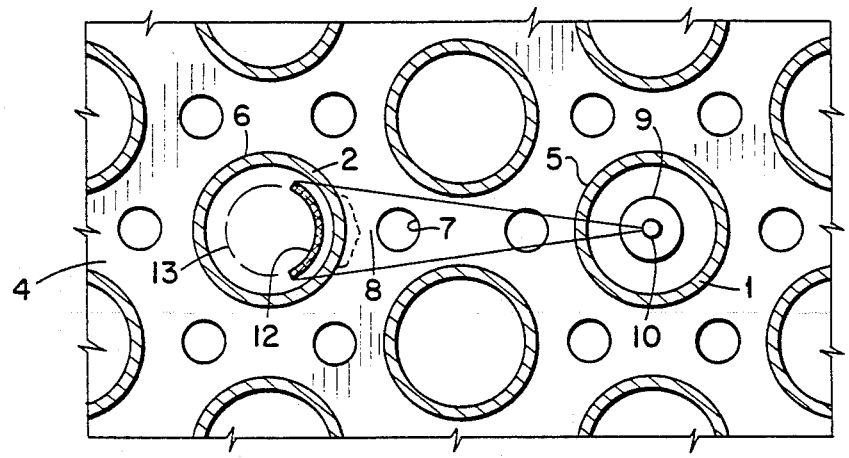

United States Patent [19]

Radcliff

[11] Patent Number: 4,567,012

[45] Date of Patent: Jan. 28, 1986

[54] DUAL ISOTOPE METHOD TO RADIOGRAPH STRUCTURES IN NUCLEAR STEAM SUPPLY SYSTEMS

[75] Inventor: Frank T. Radcliff, Chattanooga, Tenn.

[73] Assignee: Combustion Engineering, Inc., Windsor, Conn.

[21] Appl. No.: 397,296

[22] Filed: Jul. 12, 1982

[51] Int. Cl.[4] ............................................. G21C 17/00
[52] U.S. Cl. .................................. 376/245; 165/11.1; 378/54; 378/59
[58] Field of Search ..................... 378/54, 59; 376/245; 165/11 R, 11 A

[56] References Cited

U.S. PATENT DOCUMENTS

| | | | |
|---|---|---|---|
| 3,696,932 | 8/1972 | Ries et al. | 378/59 |
| 3,906,358 | 9/1975 | Stone | 378/54 |
| 3,958,120 | 5/1976 | Ward | 378/59 |
| 3,993,406 | 11/1976 | English | 378/59 |
| 3,994,173 | 11/1976 | Ward et al. | 378/59 |
| 4,228,353 | 10/1980 | Johnson | 378/54 |

*Primary Examiner*—Sal Cangialosi
*Attorney, Agent, or Firm*—Troxell K. Snyder; Arthur L. Wade

[57] ABSTRACT

Two parallel heat exchange tubes having that part of a support structure between them to be interrogated for defects. A pair of radiation sources are positioned in the one tube to straddle the interrogated support portion, and a radiographic film is positioned in the tube behind the interrogated portion.

5 Claims, 2 Drawing Figures

U.S. Patent  Jan. 28, 1986  4,567,012

DUAL ISOTOPE METHOD TO RADIOGRAPH STRUCTURES IN NUCLEAR STEAM SUPPLY SYSTEMS

TECHNICAL FIELD

The present invention relates to the nondestructive radiographic interrogation of a portion of the body of a support structure for the tubes of a bundle within a nuclear powered steam generator. More particularly, the invention relates to the nondestructive radiographic interrogation of the ligaments of a support plate between the tube holes and flow holes.

BACKGROUND ART

General

The support plates for the tubes of bundles mounted in indirect heat exchangers of nuclear powered generators are one of the myriad components requiring inspection after a period of service. If these support plates are permitted to deteriorate, lengths of the tubes they are designed to support will be vulnerable to the destructive forces of fluids passed through and over the tubes. Although creative energies are being applied to develop improved support structures, the simple drilled, or broached, plate has been used predominantly. These plates, in the order of ¾" thick, have holes formed in them for the tubes and holes through which the fluids being heated are flowed.

In service, corrosion products build up on the crevice formed between the external surface of the tubes and their holes in their support plates. Analysis of this phenomena is found throughout the prior art. It is presently sufficient to point out that these accumulations have been effective in distorting the tubes, themselves, and simultaneously applying destructive force on that portion of the support plate between the tube holes and adjacent flow holes. Periodic inspection must be made to determine the extent to which cracks have been formed in these ligaments between the tube holes and flow holes. It is in this arena that the present invention functions to improve the quality in the nondestructive radiographic interrogation of these ligaments.

Parenthetically, it is to be pointed out that more recent structural forms have been evolved as alternates to support plates. Specifically, the so-called eggcrate support structure represents the attempt to eliminate the crevice in which the corrosion products threaten the integrity of the supported tubes. Portions of these support bodies must be interrogated in the same manner as the ligaments of the plates. The problem is not confined to the specific form which will subsequently be disclosed.

Terms

In defining the ligaments as that plate portion between the tube holes and flow holes, it has become evident that there are a number of flow holes provided through support plates which actually intersect tube holes. In other words, there is no material remaining to form a ligament. This term crops up frequently in discussing the prior art and the problem of ligament interrogation.

The basic arrangement for radiographic interrogation is to place a source of radiation on one side of the portion of the support body to be interrogated and a sensitive film on the opposite side. The object of the arrangement is to penetrate the body portion under interrogation with radiation from the source and project the penetrating radiation onto the sensitive surface of the film. The result is a visual representation on the film which is evidence of any gap, crack, or defect, within the body interrogated. The uniformity of the radiation from the source which penetrates the material interrogated determines the quality of the end result as a visual record on the film.

Both the radiation source and radiographic film are moved into place with the interrogated ligament of the support plate between them. It is feasible to insert the source up into a first tube and the radiographic film up into a second tube strategically placed relative to the ligament to be interrogated. The art of utilizing the tubes for the radiation source and radiographic film is disclosed in at least Ward U.S. Pat. No. 3,958,120, issued May 18, 1976. The equipment for inserting and withdrawing both the source and radiographic film cassette will form little part of the present disclosure, as necessary as these systems are to the complete interrogation system. There is concern with the time element in operating the insertion and withdrawal equipment to achieve overall goals of inspection completion. However, the present invention is primarily concerned with the quality of the inspection or interrogation within the time frames of operation.

Problem

It has been the practice in the prior art to orient vertical tubes of the steam generator with an interrogated portion of the support structure between them. Thus, the interrogated portion of the support structure can be generally described as in a horizontal plane normal to the vertical tubes. A source of radiation has been vertically inserted up into a first of these tubes until it is even with the plane of the portion to be interrogated. A radiographic film is then inserted into the second of these tubes until it reaches a position which straddles the horizontal plane of the interrogated portion. The position of alignment has the obvious disadvantage of penetration difficulty to reach the desired area of interrogation interest, plus ambiguity as to the location of any discovered defects.

An alternative position for the source has been to place it above or below the plane of the interrogated portion in order for the radiation density through the interrogated portion to be increased and eliminate defects in portions of the body not being interrogated. This angle shot position of the source has the disadvantage that the radiation is not distributed uniformly through the interrogated portion and, consequently, has its own difficulties of interpretation on the radiograph obtained.

There is need for a procedure which provides a positional relationship between source, ligament to be interrogated, and radiographic film which will increase the uniformity of radiation density through the ligament to be interrogated and onto the film.

DISCLOSURE OF THE INVENTION

Given the orientation of two vertical tubes of a steam generator spaced from each other by the body of a support structure so that the portion of the support structure to be interrogated is between the two tubes and in a horizontal plane, the present invention contemplates placing a first source of radiation within the first tube and above the plane, and a second source of radiation in the first tube and below the plane, while a radiographic film is placed in the second tube breaching the plane, the body under interrogation being between the sources and the film in order for the radiographic film to receive an intense and uniform density of penetrating radiation through the interrogated portion.

More specifically, the invention contemplates a horizontal support plate having spaced holes transverse the plane of the plate through each of which is extended a vertical tube of a steam generator. With a ligament of the plate formed between a flow hole through the plane of the plate and one of the tube holes, a pair of radiation sources vertically aligned and positioned within the first vertical tube in order to direct a high density and uniform radiation through the flow hole-to-tube hole ligament onto the film in the second tube.

Other objects, advantages and features of this invention will become apparent to one skilled in the art upon consideration of the written specification, appended claims, and attached drawings.

BRIEF DESIGNATION OF THE DRAWINGS

Figure 1:
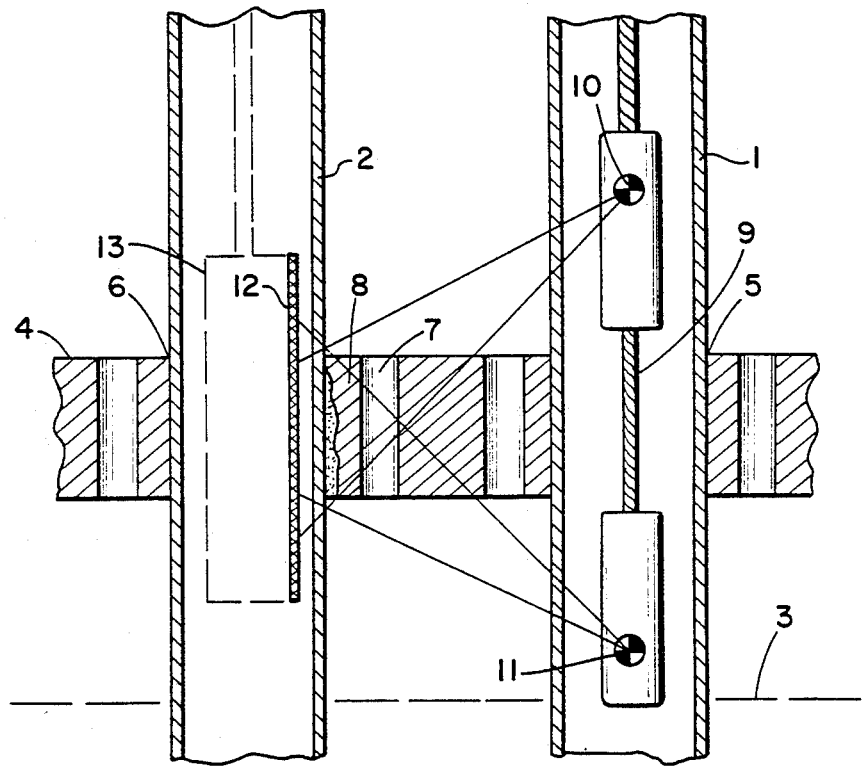

FIG. 1 is a sectioned elevation of two tubes through a supporting structure which embodies the present invention; and FIG. 2 is a plan view of FIG. 1.

BEST MODE FOR CARRYING OUT THE INVENTION

Introduction

A problem of this disclosure is to scan the extensive test reports which concluded with the invention. The minutia of the test programs, ending with the discovery of the present invention, is exhaustive and easily tends to mask the elements of the present invention, if not carefully presented.

The inspection of the support plates which form the inter-tube braces intermediate the tube ends is a formidable task. The myriad flow holes through the support plate form ligaments between themselves and the tube holes. Each tube hole forms multiple ligaments with surrounding flow holes and there is always the existance of intersection between the tube holes and flow holes which must be discriminated. Fortunately, the present invention can be disclosed by focusing upon a single ligament selected as a target for interrogation by nondestructive radiographic techniques. The technique is repeated for any number of ligaments between tube holes and flow holes, but each is simply a basic repetition of the disclosure of this application.

The basic problem of ligament interrogation is to place a radiation responsive image recording means adjacent the ligament selected for interrogation. Further, the ligament to be interrogated is positioned between the recording means and a source of gamma radiation. The complication begins with the fact that one of the tubes must be utilized to receive the recording means to position the recording means adjacent the ligament to be interrogated. Another tube must then be selected for the radiation source which will place the ligament to be interrogated between the source and the recording means. Finally, the source must be arranged so that its radiation will penetrate the interrogated ligament with sufficiently high density of radiation and with enough uniformity to provide the desired quality to evidence any defect in the ligament sharply and without ambiguity.

Before proceeding, it is to be understood that the ligament of the plate, as an intermediate tube support, is representative of any portion of a support structure which requires this nondestructive radiographic interrogation. Although the actual reduction to practice of the invention was with the ligaments of plates, and the drawings are formed around this type of support structure, there are other support structures, such as the eggcrate form, whose portions will require this type of interrogation. Therefore, the present invention will include the use of strategically placed tubes which sandwich portions of any support body which requires interrogation.

The gamma ray sources considered were iridium 192 and ytterbium 169. Iridium 192 has an equivalent energy level of about 0.45 MeV while the ytterbium 169 equivalent energy level has been determined to be about 0.27 MeV. These isotopes have been utilized in radiography programs. It was determined that these two sources achieved about the same sensitivity in radiographs made in steel approximately 0.4 inch thick. Below that thickness, radiographs made with the ytterbium 169 source had better sensitivity than those made with iridium 192, with the opposite situation existing in the larger thicknesses. An evaluation of potential shot configurations indicated a range of material thicknesses from about 0.1 inch (with an angle shot and intersecting tube and flow holes) to approximately 0.8 inch (when the source is positioned at the support plate centerline.) In this range of potential thicknesses neither isotope has a great advantage on the basis of maximum achievable sensitivity. Both sources can be obtained in about the same desired small physical size. Compared to an ytterbium 169 source of the same size, iridium 192 has about 3 times the strength, can be purchased for about 25% of the cost, and can be obtained much faster commercially. In addition, the iridium 192 isotope has more than twice the half-life of ytterbium 169. On the basis of these factors, iridium 192 was selected as the gamma ray source in the actual reduction to practice of the invention.

Three types of film were evaluated. These were Kodak Fine Grain Positive Film 7302 (FGP7302), Kodak Industrex R film DR-54 (DR-54), and Kodak Industrex M film M-5 (M-5). FGP7302 is a very slow film with a thin, rather fragile single emulsion layer. It is most useful when the background radiation level in the unit is very high and the system for positioning the film is slow. In this situation the slow film speed reduces fogging, but also increases shot time. When this film is loaded, the emultion layer must face toward the direction of the penetrating radiation. The emulsion side is difficult to discriminate in the darkroom environment, resulting in the possibility of loading the film cassettes backward.

The two remaining candidates, M-5 and DR-54, are double emulsion films which eliminate the film fogging problem. Type M-5 is faster and has been used in the past in combination with ytterbium 169 sources to speed up the shot time (because the low specific activity of this source in combination with desired small physical size results in low strength values). Type M-5 film did show more fogging than DR-54 in earlier tests. Kodak DR-54 Industrex film was the film finally selected for extensive evaluation because of its fogging characteristics, ease of dark-room handling, acceptable estimated exposure times for anticipated shot configurations, reasonable cost, availability, and suitability for standard development techniques.

A series of shot configurations were studied. The initial shot evaluated has been designated the straight shot. In this shot, the source was positioned near the midthickness of the support plate, producing radiographs of a very uniform density in the film in appropriate adjacent tubes. The disadvantage encountered with the straight shot was that major tight cracks in the ligament adjacent to the source tube could be projected on the film to such an extent that the image of small cracks from the film hole ligament could be obscured or made very difficult to interpret. This problem led to an evaluation of an angle shot in which the source was positioned outside the plate thickness. This shot was effective in eliminating the projection problem. The angle shot provided a better discrimination between cracked ligaments and intersecting tube and flow holes than the straight shot. The problem with the angle shot was the very large density variation along the length of the radiograph due to the varying distance and metal thickness between source and film. This made any interrogation of the plate midthickness ligament areas difficult. It was the conclusions drawn from the first two shots that led to the present invention.

The Supported Tubes

In FIG. 1, both the structure for interrogation and the method for operating that structure are crystalized around two heat exchange tubes as supported by the structure to be interrogated. The figure is a simple cross-sectional elevation of two representative heat exchange tubes of a bundle within a nuclear steam generator. First tube 1 and second tube 2 are oriented to extend vertically upward from a tube sheet 3 which extends horizontally across the vessel of the steam generator.

Tubes 1 and 2 extend through tube sheet 3 and are open-ended to receive fluid which has been heated by nuclear reaction. When it is time for inspecting, or interrogating, predetermined portions of the inter-tube support structure, access to the portions to be interrogated is available up through the lower open ends of tubes 1 and 2.

The inter-tube support structure for tubes 1 and 2 is depicted as extending between tubes 1 and 2 at 4. Although the inter-tube support structure may take other forms, FIG. 1 discloses it as a simple plate through which holes have been formed to receive tubes 1 and 2. Specifically, tube hole 5 receives first tube 1, and tube hole 6 receives second tube 2. It is well-established how the inter-tube support structure must have additional passages to provide flow of fluid being heated along the external surface of heating tubes 1 and 2. The plan view of FIG. 2 shows most clearly a number of these flow holes through the support structure 4, as well as other tube holes. Flow hole 7 is shown as representative of all flow holes. Although FIG. 2 indicates the presence of tubes in tube holes other than 5 and 6, the tubes in these other tube holes are not shown in FIG. 1, as they would unnecessarily clutter FIG. 1.

Flow hole 7 is spaced from tube hole 6, leaving a portion of material at 8 which has been termed a ligament of plate 4. It is this portion of the inter-tube structure which is assumed to be vulnerable to the stress induced by corrosion products formed in the crevice between second tube 2 and the wall of tube hole 6. Stressed, ligament 8 requires periodic interrogation to evaluate the status of defects which may be formed internally and/or externally within the body of the ligament. It is the object of the present invention to secure a radiographic record of this ligament 8 which will evidence the status of defects and provide a basis for decisions on subsequent remedial action.

The shortcomings of the present art have been previously discussed. If a radiation source is placed at the horizontal plane of inter-tube structure 4, penetration of ligament 8 by the radiation may record on a radiographic film in second tube 2. However, any defects, or anomalies, in that portion of the plate 4 between tube hole 5 and flow hole 7 may mask the desired image of ligament 8. Also, the density of the radiation through both the material of plate 4 between tube hole 5 and flow hole 7 may be reduced to the point where that available for ligament 8 will result in a weak radiographic image on the film in second tube 2.

Attempts have been made to increase this density by sidestepping that portion of the plate between flow hole 7 and tube hole 5. The single radiation source has been positioned above the plane of the plate 4 so that ligament 8 would receive more directly the radiation from the source for projection upon a film in second tube 2. However, the results of increasing the density by this technique include a variation of the density because of the angle at which ligament 8 receives the pentrating radiation on the vertically oriented film in second tube 2. In view of these failures of the prior art, the present invention was conceived.

Structurally, under the concepts of the invention, two sources of radiation are strategically positioned up first tube 1 in a containment capsule structure 9. In the drawing, there is shown a separate capsule structure for each radiation source 10 and 11. A single containment capsule structure could be used, but the actual reduction to practice presently utilizes a separate containment capsule structure for each source, the capsules being linked together by a flexible, metallic cable. In either event, the containment capsule structure is unitarily designated 9. An eddy current sensor is included in capsule structure 9 to give remote indication of the correct positioning of capsule 9 within tube 1. Radiation source 10 and radiation source 11 are positioned vertically up tube 1. The two sources of radiation are spaced vertically from each other and are positioned in tube 1 to place source 10 a predetermined distance above the plane of plate 4, while source 11 is maintained an equal predetermined distance below plate 4. So placed, the radiation from sources 10 and 11 each provide an angle shot to simultaneously penetrate interrogated ligament 8 with uniformly distributed radiation of satisfactorily high density. A film 12, within a cassette 13, is carried up the lower open end of second tube 2 to straddle the horizontal plane of plate 4. The film 12 is to be placed on one side of ligament 8 and closely adjacent thereto for receipt of penetrating radiation from sources 10 and 11 on the opposite side of interrogated ligament 8. The result is a very satisfactory recordation of the image of ligament 8 on the film 12. As with capsule 9, an eddy current sensor is provided for cassette 13 with which to precisely vertically straddle the horizontal plane of plate 4.

The invention, then, is first lodged in the structural arrangement of vertically aligned sources 10 and 11 in first tube 1 relative to the plane of support plate 4 so that the radiation from the sources will fall upon the film 12 in second tube 2 after penetrating the interrogated ligament 8. The invention is in the structural arrangement, as well as the process of positioning the capsuled sources up first tube 1, while the cassette 13 is positioned up second tube 2 in order to obtain a radiographic image analyzing the defects in interrogated ligament 8.

Conclusion

To dramatically outline, pinpoint, and formulate the present invention, the disclosure framing the embodiment of the invention had best be identified. The invention seeks, as a result, to obtain a comprehensive radiographic image of structure which is both vulnerable to defect and awkward to sandwiching between a source of radiation and a radiographic recording means.

The ligament of the inter-tube support structure within a nuclear steam generator becomes representative of structure difficult to reach and, yet, requiring interrogation. So much intervening structure is between the ligament and the conventional position available for radiation sources, it shields the interrogated ligament from radiation view. The present invention is in the strategic location of a plurality of radiation sources which sidestep the intervening structure to direct radiation not only directly upon the interrogated ligament, but uniformly on the radiographic film behind the ligament. The result is a radiographic record of uniform density made by radiation of sufficiently high density to make interpretation of the defects within the ligament fully identifiable.

The capsule for the radiation sources is not unique except in its structure enabling it to retain the dual sources at a fixed distance from each other. The location structure within the capsule which makes it possible to center the capsule relative to the intervening structure is not, in and of itself, unique. Nor is the cassette for the radiographic film novel, or its means for inserting the cassette and its film up into its tube. Correspondingly, the structure for determining the correct vertical position of the cassette and its film relative to the ligament is not novel. Obviously, in a structure for azimuthally orienting the film relative to the interrogated ligament does not form a part of the present invention. Again, the invention lies in the method and structure for focusing the radiation of plural sources upon awkwardly located structure to be interrogated in order to obtain a radiographic record of high quality.

From the foregoing, it will be seen that this invention is one well adapted to attain all of the ends and objects hereinabove set forth, together with other advantages which are obvious and inherent to the method and apparatus.

It will be understood that certain features and subcombinations are of utility and may be employed without reference to other features and subcombinations. This is contemplated by and is within the scope of the invention.

As many possible embodiments may be made of the invention without departing from the scope thereof, it is to be understood that all matter herein set forth or shown in the accompanying drawings is to be interpreted in an illustrative and not in a limiting sense.

I claim:

1. In a steam generator having a vessel housing a purality of open-ended tubes arranged laterally adjacent to one another and supported near their ends by a substantially continuous tube sheet extending across the vessel and supported by inter-tube structure periodically placed intermediate the tube ends, apparatus for providing a radiographic image of a portion of the inter-tube structure comprising:
   a. a pair of radiation sources spaced from each other and insertable in a first tube,
   b. and a radiation responsive image recording means insertable in a second tube adjacent that portion of the inter-tube support structure so that the support portion interrogated is between the two tubes and each source is an equal distance from the plane containing that portion of the inter-tube support to be interrogated,
   whereby the radiation penetrating that portion of the support is of uniform density in projecting the image on the radiation responsive image recording means.

2. The radiographic interrogating apparatus of claim 1, in which,
   the tubes of the steam generator are oriented vertically,
   and the inter-tube support structure is a flat plate having a flow hole spaced from the tube hole of the second tube to form a ligament to be interrogated.

3. The apparatus of claim 2, in which,
   each of the sources is iridium 192 which emits radiation in the form of gamma rays,
   and the radiation responsive image recording means is Kodak DR-54 Industrex film.

4. In a steam generator having a vessel housing a plurality of open-ended tubes arranged laterally adjacent to one another and supported near their ends by a substantially continuous tube sheet extending across the vessel and supported by inter-tube structure periodically placed intermediate the tube ends, the method of interrogating a predetermined portion of the inter-tube structure for defects comprising the steps of:
   a. inserting two radiation sources which are spaced from each other into a first tube to position each of the sources a predetermined vertical distance on each side of the plane of the inter-tube support structure portion,
   b. and inserting a radiation responsive image recording means in a second tube adjacent the portion of the inter-tube support structure so that the support portion interrogated is between the two tubes to receive a uniform density of radiation from the two sources through the penetrated portion.

5. The method of claim 4, including,
   the steps of removing the sources of radiation and the image recording means to obtain the radiographic record of the interrogated portion of the inter-tube structure.

* * * * *